(12) United States Patent
Mejlhede et al.

(10) Patent No.: US 7,455,325 B2
(45) Date of Patent: Nov. 25, 2008

(54) CONNECTING ELEMENT COMPRISING A FIRST BODY AND A METHOD FOR INJECTION MOULDING A CONNECTING ELEMENT

(75) Inventors: Signe Mejlhede, Svinninge (DK); Grete Kornerup, Vipperød (DK)

(73) Assignee: Unomedical A/S, Birkerod (DK)

( * ) Notice: Subject to any disclaimer, the term of this patent is extended or adjusted under 35 U.S.C. 154(b) by 88 days.

(21) Appl. No.: 11/024,892

(22) Filed: Dec. 29, 2004

(65) Prior Publication Data

US 2005/0142945 A1 Jun. 30, 2005

Related U.S. Application Data

(63) Continuation-in-part of application No. PCT/DK2004/000100, filed on Feb. 12, 2004, and a continuation-in-part of application No. 10/437,488, filed on May 13, 2003, now abandoned.

(51) Int. Cl.
*F16L 13/10* (2006.01)
*F16L 13/11* (2006.01)
*F16L 47/02* (2006.01)

(52) U.S. Cl. ............... 285/286.1; 285/285.1; 285/286.2; 285/293.1; 285/423; 604/533

(58) Field of Classification Search ................. 285/423, 285/285.1, 286.1, 286.2, 293.1; 604/533
See application file for complete search history.

(56) References Cited

U.S. PATENT DOCUMENTS

| | | | |
|---|---|---|---|
| 3,469,579 A | 9/1969 | Hubert | |
| 4,509,945 A | 4/1985 | Kramann et al. | |
| 4,693,710 A | 9/1987 | McCool | |
| 4,695,276 A * | 9/1987 | Shinno et al. | 604/533 |
| 4,776,849 A * | 10/1988 | Shinno et al. | 604/533 |
| 4,790,829 A * | 12/1988 | Bowden et al. | 604/244 |
| 4,824,145 A | 4/1989 | Carlsson | |
| 4,874,377 A | 10/1989 | Newgard et al. | |
| 4,878,900 A | 11/1989 | Sundt | |
| 5,167,647 A | 12/1992 | Wijkamp et al. | |
| 5,199,947 A | 4/1993 | Lopez et al. | |
| 5,586,977 A | 12/1996 | Dorsey | |
| 5,611,576 A | 3/1997 | Guala | |
| 5,735,813 A * | 4/1998 | Lewis | 604/43 |
| 5,776,116 A * | 7/1998 | Lopez et al. | 604/533 |
| 5,782,505 A | 7/1998 | Brooks et al. | |

(Continued)

FOREIGN PATENT DOCUMENTS

DE 297 12 676 U1 11/1997

(Continued)

*Primary Examiner*—James M Hewitt
(74) *Attorney, Agent, or Firm*—Merchant & Gould P.C.

(57) ABSTRACT

A medical connector for connecting a tube with a medical device and having a through-going bore which at one end of the connector comprises a cavity for permanently attaching the end of the tube to the connector and which at least at the end of the connector comprises an inner part and an outer part; the inner part and the outer part being integrally connected, the outer part being made from a thermoplastic material which is resistant to changes when subjected to the influence of a disinfectant and the inner part being made from a thermoplastic material which is compatible with a soft glue and a method for injection moulding such connectors.

12 Claims, 5 Drawing Sheets

U.S. PATENT DOCUMENTS

| | | |
|---|---|---|
| 5,803,509 A | 9/1998 | Adams |
| 5,830,401 A | 11/1998 | Prichard et al. |
| 6,017,319 A | 1/2000 | Jacobsen et al. |
| 6,156,054 A | 12/2000 | Zadno-Azizi et al. |
| 6,260,890 B1 | 7/2001 | Mason |
| 6,273,478 B1 | 8/2001 | Benett et al. |
| 6,290,688 B1 | 9/2001 | Lopez et al. |
| 6,332,874 B1 | 12/2001 | Eliasen et al. |
| 6,575,959 B1 | 6/2003 | Sarge et al. |
| 6,651,956 B2 | 11/2003 | Miller |
| 2004/0100093 A1* | 5/2004 | Leigh-Monstevens ....... 285/222 |
| 2005/0059958 A1* | 3/2005 | Lessard et al. ............. 604/533 |
| 2006/0259012 A1* | 11/2006 | Propp et al. ................. 604/533 |

FOREIGN PATENT DOCUMENTS

| | | |
|---|---|---|
| EP | 0 151 519 | 8/1985 |
| EP | 0 753 323 | 1/1997 |
| EP | 0 953 365 A2 | 11/1999 |
| EP | 0 775 501 | 6/2002 |
| GB | 1 437 352 | 5/1976 |
| GB | 2 084 298 | 4/1982 |
| WO | WO 98/35808 | 8/1998 |
| WO | WO 00/73040 A1 | 12/2000 |

* cited by examiner

CONNECTING ELEMENT COMPRISING A FIRST BODY AND A METHOD FOR INJECTION MOULDING A CONNECTING ELEMENT

This application is a Continuation-in-Part of International Application No. PCT/DK2004/000100 filed Feb. 12, 2004 and a Continuation-in-Part of U.S. application Ser. No. 10/437,488 filed on May 13, 2003 and now abandoned, which claims priority on application Ser No. PA200300207 filed Feb. 12, 2003, which application is incorporated herein by reference.

BACKGROUND

This invention relates to a medical connector for connecting a tube to a medical device such as an insulin delivery device.

Such connectors are typically provided with means such as Luer-Lock type means for connecting the end of the connector which is opposite to the end at which the tube is connected to the connector, to the medical device so as to allow the connector to be disengaged from said device, this allowing the medical device and/or the connector including the tube to be replaced.

EP 0 753 323 A1 describes a coupling for joining the ends of two tubes, said coupling comprising a male part and a female part, both the male and female part having means for attachment of the end of a tube.

EP 0 151 519 describes a tube coupling comprising a male part and a female part, both the male part and the female part comprising a tapered tube connecting portion which is adapted to be inserted into the end of a tube.

EP 0 775 501 B describes a female coupling element of the Luer-Lock type comprising an outer tubular body which is made of a relatively rigid moulded thermoplastics material and which can be connected with a complimentary male coupling element, and an inner sleeve which is made of a softer moulded thermoplastics material which at one end is fitted within the outer body in such a manner that the two parts are freely rotatable relative to each other and at the opposite end comprises a cavity for connection to e.g. a tube.

Furthermore, medical connectors consisting of a single plastics material and manufactured by injection moulding are known.

Such medical connectors comprise a through-going opening, one end of said connector being adapted to be connected with the end of a tube by gluing so as to form a permanent connection and the opposite end comprising a part of a Luer-Lock type connection for connecting the connector to a medical device such as an insulin pump.

Due to the fact that an injection moulding process is a simple manufacturing method, such medical connectors can be manufactured at low costs. However, these medical connectors suffer from a drawback.

Thus, prior to the use of a medical connector it has to be disinfected which ordinarily is effected by wiping it with a liquid disinfectant such as ethyl alcohol.

Such a treatment may cause stresses in some plastics material to be released during physical strain and may result in the formation of cracks which bring about leaks.

The selection of a plastics material which is resistant to the influence of disinfectants may cause another problem, viz. that the permanent connection of the tube end to the connector has to be effected by means of a hard glue. The use of a hard glue in contrast to a soft glue results in an inflexible connection between the tube and the connector and may result in a leakage due to repeated bending of the tube in the zone adjacent to the glue.

In the previously known connectors composed of two plastics materials, such as those described in EP 0 775 501 B, the two parts have to be made separately and be assembled afterwards. This increases the production costs compared to connectors which can be injection moulded in one-piece.

SUMMARY

The object of the present invention is to provide a medical connector which can be manufactured in large quantities at low costs and which is more resistant to leakage than the prior art medical connectors.

According to the invention there is provided a medical connector for connecting a tube with a medical device and having an upper end, a lower end and a through-going opening which at the upper end of the connector comprises a cavity for permanently attaching the end of the tube to the connector and which at least at said end of the connector comprises an inner part having an upper delimiting surface and an outer part having an upper delimiting surface; the inner and outer parts being integrally connected, the outer part being made from a thermoplastics material which is resistant the influence of a disinfectant and the inner part being made from a thermoplastics material which is compatible with a soft glue which connector is characterized in that the upper delimiting surface of the outer part projects proud of the upper delimiting surface of the inner part.

The advantage of having the upper delimiting surface of the outer part projecting proud of the upper delimiting surface of the inner part is that it is easier to effectively seal of the inner part from any disinfectants e.g. by use of a glue. If disinfectants come in contact with the inner part there is a risk that small cracks will appear. During repeated wiping such a small crack can spread though the material a reach the area where the connection is made thus resulting in a possible fragile connection.

The term integrally connected is to be understood as the two parts are connected in such way that they are unable to rotate independently around the longitudinal axis.

This new type of connectors is easy and cheap to produce. It is resistant to the mandatory disinfection prior to use and it has a flexible but permanent attachment of the tube to the connector.

According to the invention there is further provided a method for injection moulding of a connector of the above mentioned type comprising the steps of injecting a plastics material which is compatible with a soft glue into a mould having a cavity of the desired shape and a core of the desired shape for forming a cavity in the connector for permanently attaching an end of a tube injecting a plastics material which is resistant to changes when subjected to the influence of a disinfectant into a mould having a cavity of the desired shape, a core for creating a through-going opening using a part of the surface of the firstly injected plastics material as part of the mould receiving the secondly injected plastics material.

In one embodiment of the invention the connector comprises means for connecting the connector to a medical device such as an insulin pump, said means preferably being in form of a Luer-Lock type, and more preferably the means are capable of receiving the male part of the Luer-Lock type.

In a preferred embodiment the term integrally connected further implies that the two parts are unable to move independently along the length axis.

Preferably the connector comprises means for getting a better hold of the connector, which can be advantageous when connecting or disconnecting the connector to a medical device. Said means can be but are not limited to a groove, a ribbon, a rim, preferably the means are in form of a groove.

Preferably said means are placed in the same end as the tube is supposed to be attached.

In another embodiment of the invention the inner part and the outer part of the connector are capable of rocking relative to each other thereby providing a more flexible but still permanent connection to the tube. This reduces the risk of leakage even further.

In a preferred embodiment the cavity for permanently attaching the end of the tube has an increasing diameter towards the upper end of the connector, preferably a part of the cavity has a conical shape. Preferably, the conical part forms an angle of at least 15 degrees relative to the central axis, preferably the angle is between 20 and 25 degrees.

In another embodiment the cavity of the outer part at the end receiving the tube also has an increasing diameter towards the outer end. Preferably at least a part of the cavity of the outer part has a conical shape.

By using a conical-shaped cavity of the inner part and/or a cavity of the outer part with an increasing diameter an even more flexible connection between the connector and the tube can be achieved. Further, the increasing diameter leaves more room for the soft and elastic glue and makes it possible to effectively seal off the inner part from any disinfectant thus reducing the risk of cracks in the connection.

In a preferred embodiment the diameter of the cavity of the inner part is adapted to the diameter of the tube supposed to be permanently connected with the connector.

Preferably the connector is constructed in such way that the inner part at least in the area of connection between the connector and the tube is unable to come into contact with the disinfectants. Preferably the plastics material of the inner part is selected exclusively from its gluing properties i.e. it is compatible with a soft glue.

In one embodiment of the invention the delimiting part of the edge is flush with the delimiting edge of the outer part or even broaches there around and encloses portions of the outer faces of the outer part. In this case what matters is that a sealing is provided to prevent the liquid from penetrating from the outside and into the connecting area between the tube and the inner part.

In another embodiment the outer part is moulded in such way that it encloses the outer faces of the inner part so that during wiping with a disinfectant connection between the disinfectant and the inner part of the connector cannot be provided.

The connector with its permanently attached tube is preferably intended for use for infusion kits where the luer lock is mounted to an insulin pump, while the tube as such is connected to a syringe and an infusion part.

In another preferred embodiment the inner part and/or the outer part comprises fasteners for fastening the inner part to the outer part or visa versa, more preferably the inner part has retention devices and the outer part has grooves adapted to receive said retention devices. In an even more preferred embodiment the retention devices are mounted on the outside of the inner part and thereby providing a good retention between the inner part and the outer part ensuring that the inner part cannot be loosened.

In another embodiment the inner part and the outer part are connected and/or held together by means of a glue.

In another preferred embodiment the inner part, the glue and an area of the tube are capable of forming an integral chemical connection.

Preferably the soft glue used in the permanent connection between the tube and the connector as a minimum has contact to both the tube and the inner part. It is of no consequence whether the glue further has contact to the outer part or not, it is only important that the connection has an inner area which is unable to come into contact with the disinfectant used to wipe the connector prior to use.

In a preferred embodiment the through-going bore of the outer part has a central axis which is axially parallel and coincident with the central axis of the inner part.

In a preferred embodiment both the inner part and the outer part are made of a thermoplastic material. In a more preferred embodiment the inner part is made of an amorphous plastics material, preferably with a molecular structure in which the chains are positioned randomly.

In a preferred embodiment the inner part is made of ABS. ABS is made of the monomer components acrylic nitrile, butadiene and styrene. Each of the three structural units adds valuable properties to the material. Acrylic nitrile is responsible for the resistance and dimensional stability in heat. Butadiene equips the material with tenacity and makes it resistant to impacts, while styrene serves to ensure the rigidity of the material and easy processability. ABS tolerates a number of acids, bases and oils with the proviso, however, that the level of internal stresses is very low. There are a number of solvents that can dissolve ABS. Other suitable amorphous plastics materials include e.g. polycarbonate, polystyrene, acrylic plastics, poly-methyl-methacrylate and PVC.

In another preferred embodiment the outer part is made of a plastics material also being a thermoplastics material and composed of at least one partially plastics material, preferably a polypropylene is used. Polypropylene is a partially crystalline plastics material in which the molecule chains are located in parallel with each other and form rather closely packed areas, the so-called crystallites. Polypropylene is a thermoplastics material with an attractive balance between thermal and chemical resistance and good mechanical and electrical properties. Furthermore, polypropylene is immune to bacteria and fungi. Additionally polypropylene is a plastics material having a very wide-ranging resistance to chemicals. It is resistant to salts, acids, bases (inorganic) and alcohols and some oils. In principle, it is the crystallite that is decisive to the resistance to chemicals. Also other materials can be used for the outer part e.g. polyamide, polyethylene, polyethylene-ether-ketone (PEEK).

A crystalline plastics material is characterized in that the molecules are situated closely adjoining each other whereby the intermolecular forces act more strongly and more energy is to be supplied in order to overcome it. In practice this means that crystalline plastics/partially crystalline plastics generally have a higher temperature of vitrification and a higher melting point than amorphous materials. The crystalline areas in the material have a distributing effect on light and therefore crystalline and partially crystalline plastics have a milky appearance.

A thermoplastics material has the characteristic feature that it exhibits three different, more or less sharply delimiting state areas as a function of the temperature, viz. a solid state, a rubber elastic state and a viscous state. Upon heating the material becomes soft and assumes a rather more solid structure upon cooling and, in principle, it is possible to reshape it several times.

A suitable glue for use in accordance with the present invention is an acrylated urethane based glue such as Loctite® product 3201.

The following physical, mechanical properties apply to a soft glue versus a hard glue.

|  | Soft glue | Hard glue |
| --- | --- | --- |
| Extension at break | 120%-240% | 0%-50% |
| Hardness shore D | D25-D60 | D65-D90 |

In a preferred embodiment the connector is adapted to receive means for supporting the attachment of the tube. Said means are suitable for securing the tube to the connector until the glue is hardened.

During attachment of the tube to the connector it is preferred to have a final hardening after the glue is mounted between the connector and the tube. Further it is preferred that the connector is adapted to trap and secure the tube until the glue has set.

The invention also relates to an infusion unit manufactured from the connector and wherein the end opposite to the tube is connected to an insulin pump by means of a luer-lock and wherein a soft glue is used to connect the tube to the connector.

In a preferred method of producing said connectors a plastics material which is compatible with a soft glue is injected into the mould under a suitable pressure for providing the inner part, subsequently under a suitable second pressure a plastics material being resistant to changes when subjected to the influence of a disinfectant is injected into the mould. Following such moulding of the connector, said moulding taking place e.g. in accordance with principles like the ones given in patent No. WO 00/73040 and WO 98/35808, an opening of the mould takes place and the connectors are ejected from their cores. Optionally a subsequent assembly process between the connector and a tube takes place as described above by means of a soft glue.

DESCRIPTION OF THE DRAWINGS

In the following a preferred embodiment of the invention will be described with reference to the figures.

DETAILED DESCRIPTION

Figures 1A, 1B:
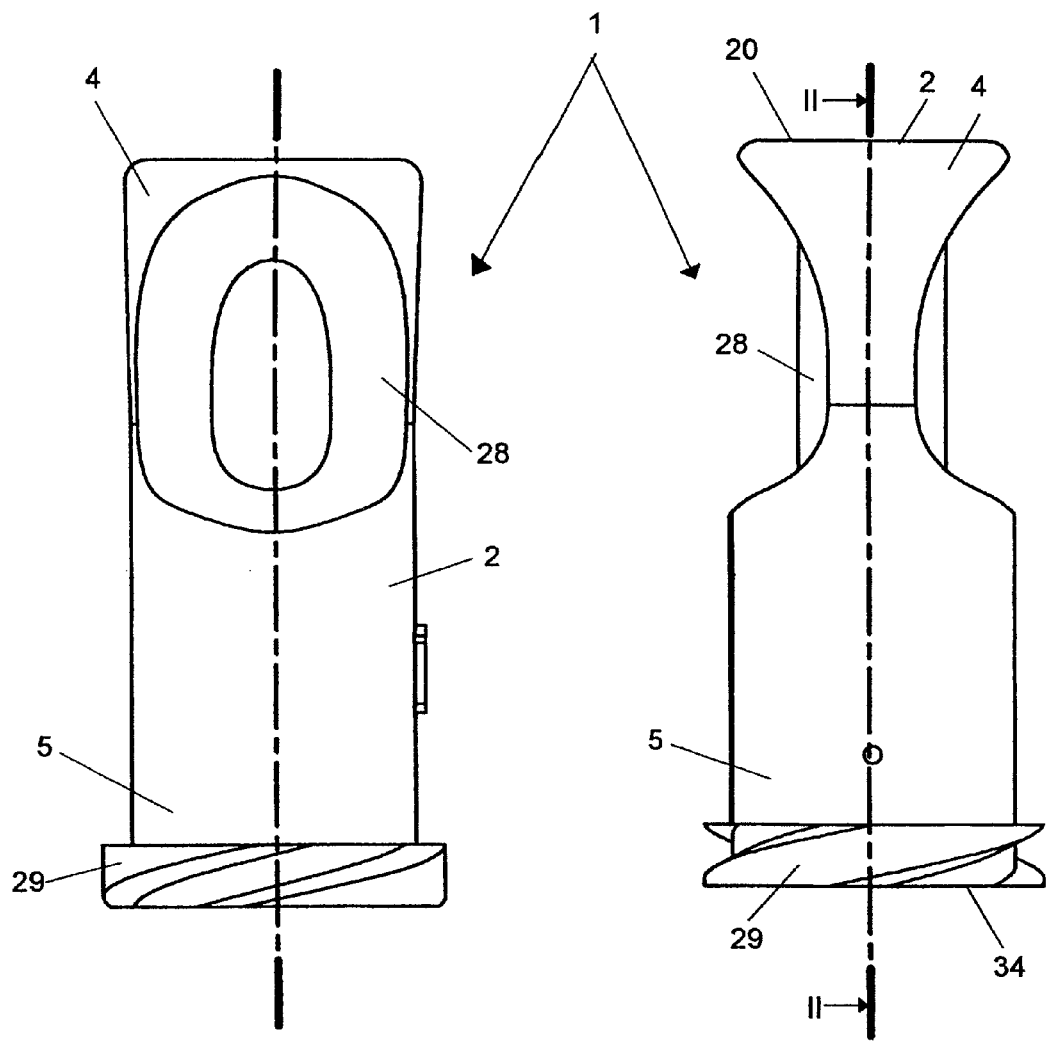
FIGS. 1A-B show an example of a connecting element according to the invention seen from two different sides.

FIGS. 1A and 1B show a connector 1, seen from the side in a first position and turned by 90°. The connector, see also FIG. 2, comprises an outer part 2 which is preferably made of a thermoplastics material that is chemically resistant to disinfectant such as ethyl alcohol. The outer part comprises an end 4 for receiving a tube and an end 5 for connecting to a medical device such as an insulin pump. The end 4 for receiving a tube comprises a cavity 6 as it is also seen in the sectional view in FIG. 2.

The end 5 for connecting to a medical device comprises a luer lock 21 in which a male luer-lock is preferably used. Finally the end 5 comprises an external double-thread 29 for being mounted to preferably an insulin pump. The outer shape of the connector 1 is such that it is essentially cylindrically shaped, but wherein the end 4 for receiving the tube has a narrowed portion for providing an oval narrowing area 28. This serves to improve the gripping around the connector 1 during handling thereof. The outer part 2 has an outer essentially plane upper delimiting face 20. The distance from this and down to the lower delimiting face 34 is within the range 17 mm.

Figure 2:
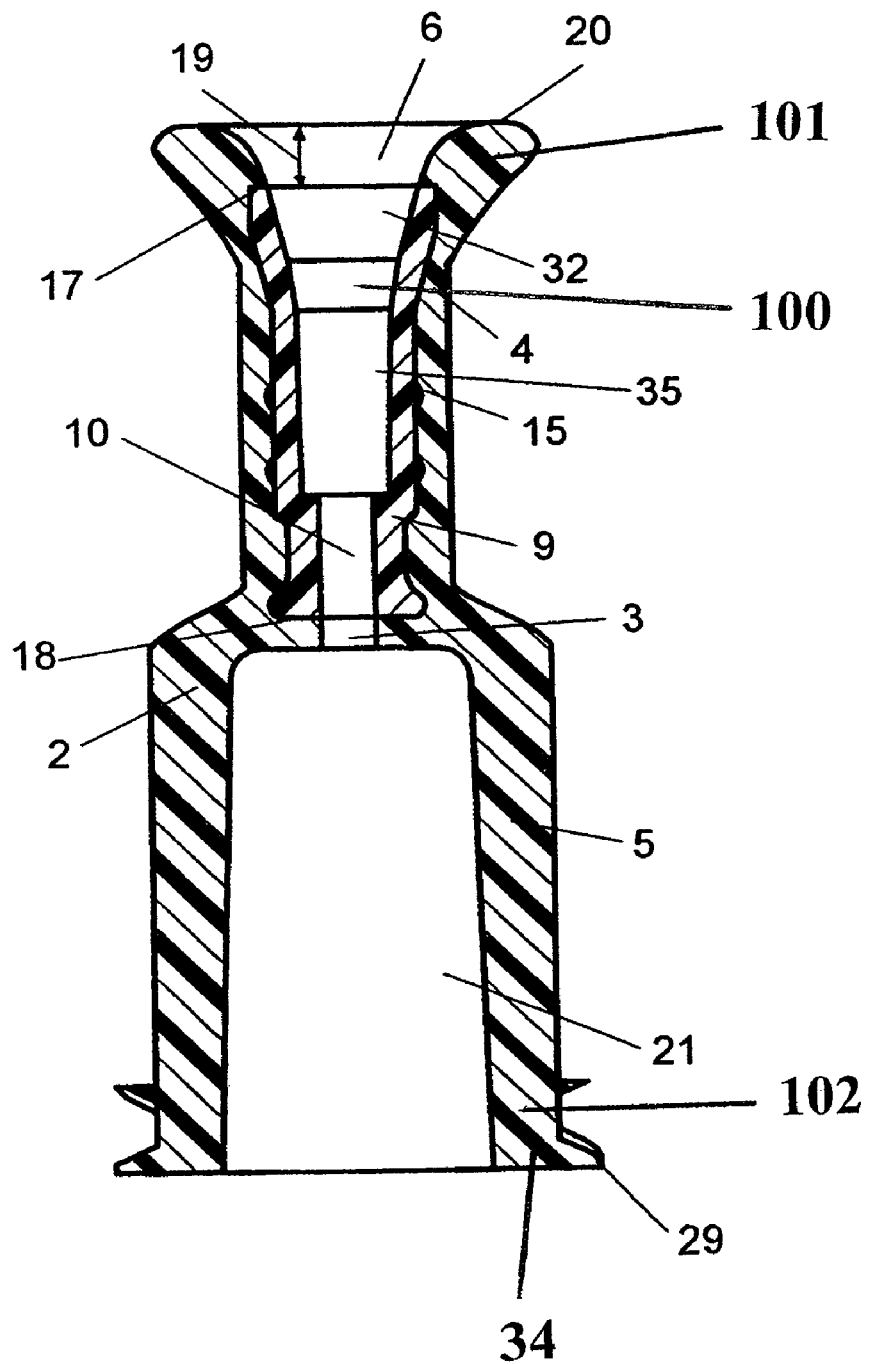
FIG. 2 is a sectional view along II-II in FIG. 1A.

FIG. 2 is a sectional view wherein the joining between the two elements that constitute the connector 1 viz. the outer part 2, the inner part 9, the upper end (101) and the lower end (102) will appear. The outer part is manufactured such that there is liquid communication throughout its entire passage and it comprises axially a passage throughout its entire interior, wherein, in its end 5, it has such shape that it forms a luer lock 21. From said luer lock 21 an axial opening 3 to the cavity 6 is provided. The central axis of the opening 3 is axially parallel and coinciding with a through-going opening 10 provided in the inner part 9. In the opposite end of the inner part 9 there is a section called the connector part 32 for the tube which is configured with side faces that diverge outwards towards an upper delimiting face 17 of the inner part, where said delimiting face 17 is of plane configuration.

In the area between the tube connector part 32 and the otherwise cylindrically shaped opening 10 the interior area 35 and a further essentially conically shaped connecting area that may also constitute a part of the tube connector part and serve as glue reservoir are situated. The interior area is situated so that the glue ensuring connection between the tube and the inner part cannot be in liquid communication with the exterior of the connector. The inner part 9 is located so that its upper delimiting face 17 of the inner part is located at a distance retracted from the upper delimiting face 20 of the outer part 2. It should further be mentioned that the inner part 9 has on its outer circumference retention devices 15 e.g. in form of studs or wings that serve as undercuts whereby good gripping is ensured during moulding between the inner part 9 and the outer part 2.

Figure 3:
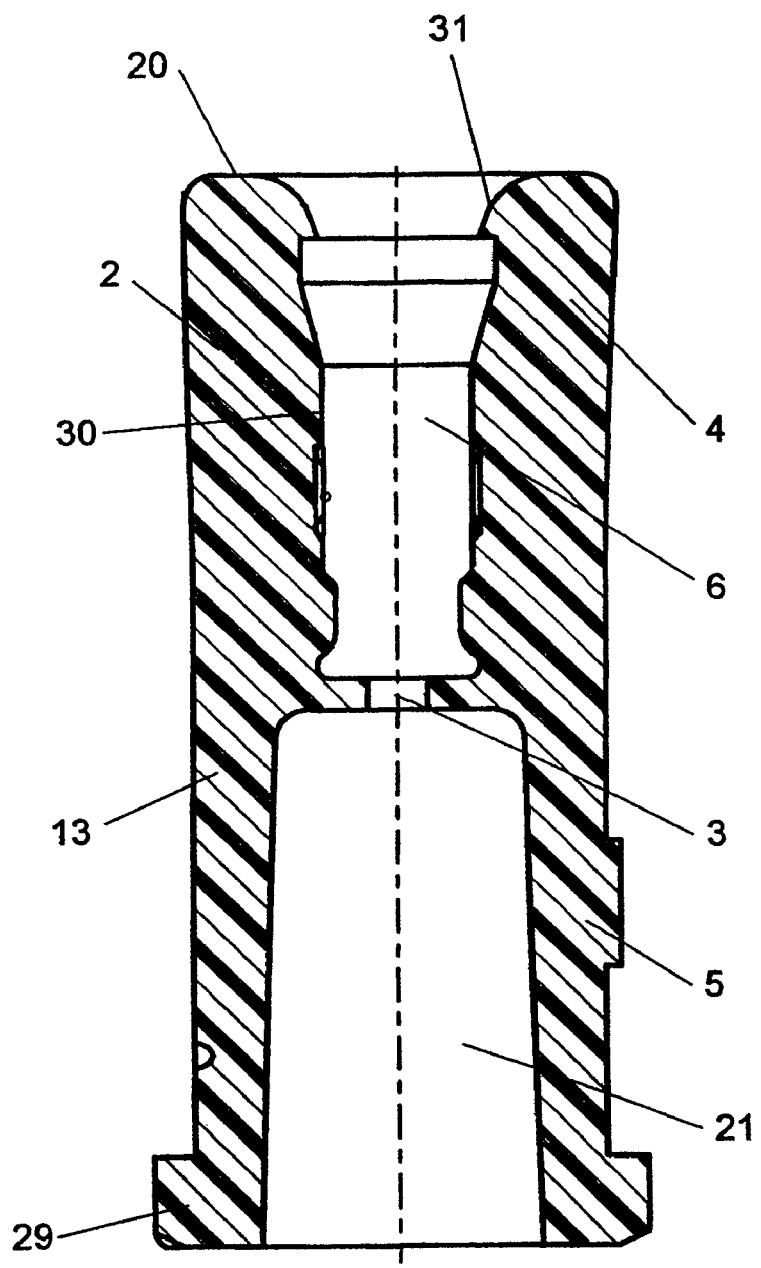
FIG. 3 is a sectional view of the outer part in detailed form.

The outer part 2 will be described with reference to FIG. 3. The outer part 2 comprises as mentioned an essentially outer cylindrically shaped sleeve having essentially three cavities; a cavity in the end 5 comprising a luer lock 21 and preferably a male luer lock from which there is connection via a central opening 3 to the cavity 6 in the end of the outer part 2 for attaching the tube which interior faces are shaped to be essentially congruent with the outer faces of the inner part. The outer part 2 is manufactured from a chemically resistant material 13, whereby no stresses are released when it is wiped with e.g. ethyl alcohol.

Figure 4:
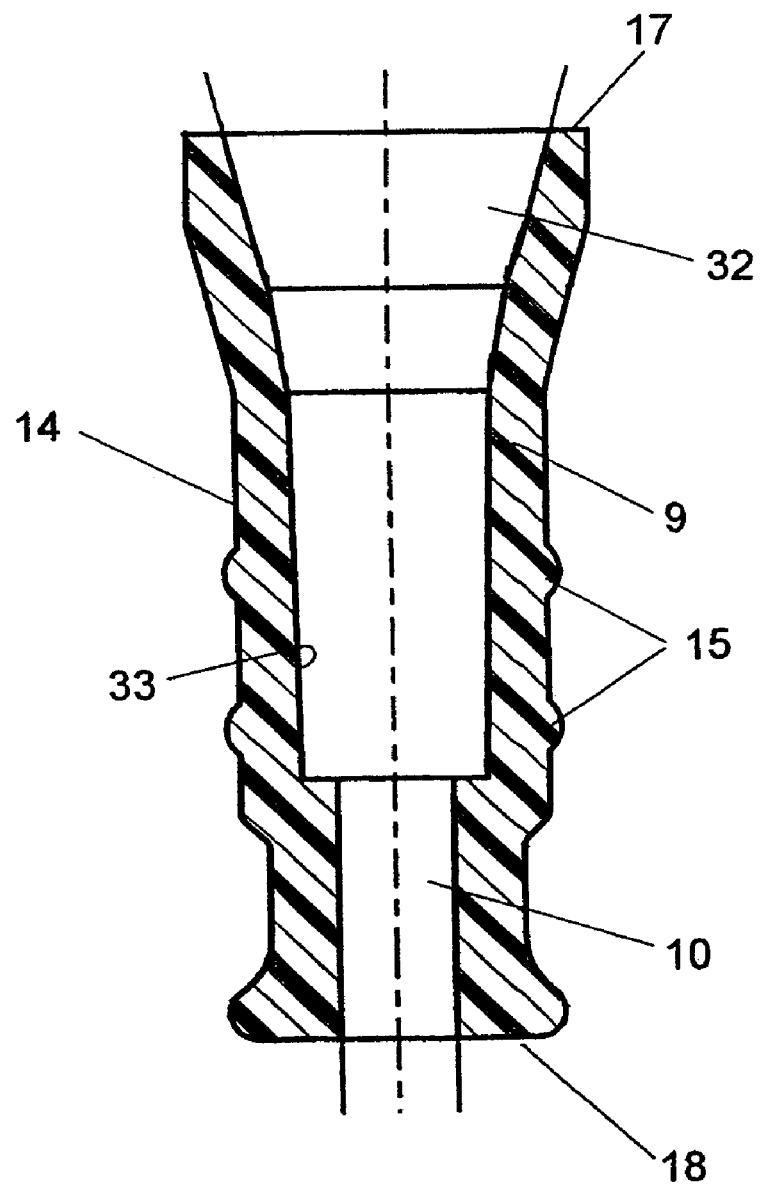
FIG. 4 is a sectional view of the inner part in detailed form.

The inner part 9 will be described with reference to FIG. 4. It also comprises a sleeve-like construction, its outer walls 14 being essentially cylindrical with various pouches/retention devices mounted thereon for providing good retention between the inner part and the outer part.

The cavity of the inner part comprises essentially four areas, viz. a through-going opening 10 in communication with the inner area 35 being an essentially cylindrical area having a length of essentially about 3 mm and with a somewhat larger diameter than the opening 10; a conical area of about 1 mm forming the connection between the inner area and the tube connector part 32; and said tube connector part constituting the upper part of the inner part 9. This tube connector part is configured such that the walls diverge outwards towards the upper delimiting face 17 of the inner part 9 said face 17 being of essentially plane configuration. As mentioned the outer walls of the inner part also comprise retention devices 15.

Figure 5:
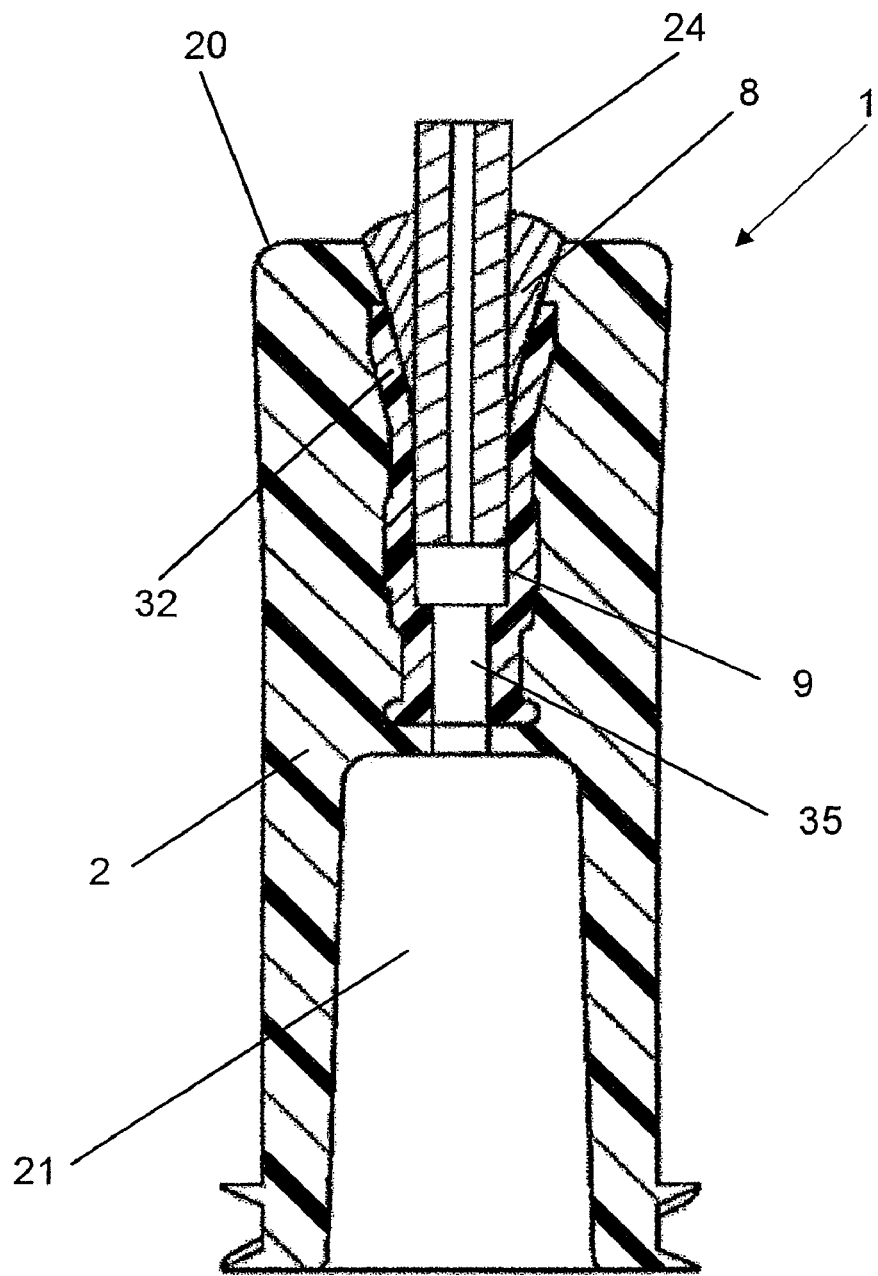
FIG. 5 shows the disclosures of FIG. 2 with a plastics tube mounted in the inner part.

The connection between the tube and the inner part including the tube connector part 32 that may also be an area where the glue bonds and seals the remaining entrance, will be described in further detail with reference to FIG. 5. It shows the joint between a connector 1 and a tube 24, wherein a section has been made through the connecting element and the tubular element. A luer-lock is shown and opposite to that the tubular element is located in the inner part 9 of the connecting element corresponding to the inner area 35. It is noted in this context that the tube connector part 32 is situated so that its upper delimiting face is located at a distance retracted from the upper delimitating face 20 of the outer part. When the tube seizes the tube connector part 32, and wherein— between the outer face of the tube 24 and the inner face of the tube connector part 32—attachment means 8 are located in the form of a soft glue, the risk of chemicals, if any, used for wiping the outer face of the outer part penetrating downwards to the inner area 35 of the inner part as such will be small due, on the one hand to said distance and, on the other hand, to the sealing properties of the glue. This is essential since the inner part is manufactured precisely from a plastics material that provides good connection to the tube when a soft glue is selected. This plastics material is not necessarily resistant to the material used for wiping. Conversely, a material that tolerates wiping with chemicals, including e.g. ethyl alcohol can be used for the outer part.

It should be noted with regard to soft glue that it is inherently more flexible than hard glue. A soft glue is used precisely in order to enable the plastic tube to retain its flexibility in the in-use situation.

The invention claimed is:

1. A medical connector for connecting a tube with a medical device and having an upper end, a lower end and a through-going opening which at the upper end of the connector comprises a cavity for permanently attaching the end of the tube to the connector and which at least at said end of the connector comprises an inner part having an upper delimiting surface and an outer part having an upper delimiting surface, the inner and outer parts being integrally connected, the outer part being made from a thermoplastic material which is resistant to the influence of a disinfectant and the inner part being made from a thermoplastic material which is compatible with a soft glue wherein the upper delimiting surface of the outer part projects proud of the upper delimiting surface of the inner part and:
    (i) the tube is attached permanently in the cavity of the inner part with a soft glue, wherein the glue is located between the outer surface of the tube and an essentially conically shaped connecting area of the cavity;
    (ii) the inner part and outer part are connected in such a way that they are unable to rotate around the longitudinal axis; and
    (iii) the inner part is unable to come in contact with disinfectants used to wipe the connector prior to use.

2. A medical connector according to claim 1, wherein the thermoplastic material for the inner part is an amorphous plastic material.

3. A medical connector according to claim 1, wherein the thermoplastic material for the inner part is an acrylonitrile butadiene styrene (ABS) material.

4. A medical connector according to claim 1, wherein the thermoplastic material for the outer part is an at least partially crystalline material.

5. A medical connector according to claim 4, wherein the thermoplastic material for the outer part is a polypropylene.

6. A medical connector according to claim 1, wherein the outer walls of the inner part are sheathed by the outer part and comprise retention devices.

7. A medical connector according to claim 1, wherein the inner part is an essentially rotationally symmetrical body with a rotationally symmetrical through-going opening.

8. A medical connector according claim 1, wherein the cavity for permanently attaching the end of the tube has an increasing diameter towards the upper end.

9. A medical connector according to claim 8, wherein the generatrix of the conically shaped connecting area forms an angle of at least 15 degrees relative to a central axis.

10. A medical connector according claim 1, wherein the outer part at the upper end has a cavity with a diameter increasing towards the upper delimiting surface.

11. A medical connector according to claim 1, wherein the connector comprises a luer-lock.

12. An infusion device comprising a connector according to claim 1, wherein the lower end of the connector is connected to an insulin pump and the upper end is connected to a plastic tube.

* * * * *

UNITED STATES PATENT AND TRADEMARK OFFICE
CERTIFICATE OF CORRECTION

| | | |
|---|---|---|
| PATENT NO. | : 7,455,325 B2 | Page 1 of 1 |
| APPLICATION NO. | : 11/024892 | |
| DATED | : November 25, 2008 | |
| INVENTOR(S) | : Mejlhede et al. | |

It is certified that error appears in the above-identified patent and that said Letters Patent is hereby corrected as shown below:

Title Page Insert
Item --(30)     Foreign Application Priority Data

Feb. 16, 2005     (DK)  ……………………….. PA200300207--

Signed and Sealed this

Seventeenth Day of February, 2009

JOHN DOLL
*Acting Director of the United States Patent and Trademark Office*